(12) United States Patent
Capello et al.

(10) Patent No.: US 8,350,910 B2
(45) Date of Patent: Jan. 8, 2013

(54) OPTICAL DEVICE FOR MOTOR VEHICLES, FOR DETECTING THE CONDITION OF THE ROAD SURFACE

(75) Inventors: Davide Capello, Orbassano (IT); Nereo Pallaro, Orbassano (IT); Luca Liotti, Orbassano (IT); Luca Guglielmetto, Orbassano (IT)

(73) Assignee: C.R.F. Società Consortile per Azioni, Orbassano (Torino) (IT)

( * ) Notice: Subject to any disclaimer, the term of this patent is extended or adjusted under 35 U.S.C. 154(b) by 516 days.

(21) Appl. No.: 12/624,102

(22) Filed: Nov. 23, 2009

(65) Prior Publication Data

US 2010/0141765 A1    Jun. 10, 2010

(30) Foreign Application Priority Data

Dec. 9, 2008 (EP) .................................. 08425784

(51) Int. Cl.
*G08G 1/00* (2006.01)
(52) U.S. Cl. ........................................ 348/148; 382/104
(58) Field of Classification Search .................. 348/149, 348/148; 382/104
See application file for complete search history.

(56) References Cited

U.S. PATENT DOCUMENTS

| | | | | | |
|---|---|---|---|---|---|
| 5,218,206 | A | * | 6/1993 | Schmitt et al. | 250/339.11 |
| 5,497,100 | A | * | 3/1996 | Reiser et al. | 324/643 |
| 5,586,028 | A | * | 12/1996 | Sekine et al. | 701/1 |
| 2003/0001509 | A1 | * | 1/2003 | Leleve | 315/77 |
| 2004/0204812 | A1 | * | 10/2004 | Tran | 701/80 |
| 2006/0050270 | A1 | * | 3/2006 | Elman | 356/326 |
| 2006/0076495 | A1 | * | 4/2006 | Dupont et al. | 250/339.11 |
| 2007/0000659 | A1 | * | 1/2007 | Schlanger et al. | 165/202 |

FOREIGN PATENT DOCUMENTS

| | | |
|---|---|---|
| DE | 40 08 280 | 3/1990 |
| DE | 40 40 842 | 12/1990 |
| DE | 41 33 359 | 10/1991 |
| DE | 298 25 238 | 1/2007 |
| DE | 10 2004 001 046 | 8/2008 |
| EP | 1 635 163 | 8/2005 |
| WO | 2004/034349 | 4/2004 |

* cited by examiner

Primary Examiner — Christopher S Kelley
Assistant Examiner — Zhen Jessica Li
(74) Attorney, Agent, or Firm — Nixon & Vanderhye, PC

(57) ABSTRACT

An optical device for motor vehicles, designed to detect the condition of the road surface, comprises a unit for the emission of electromagnetic radiation in the direction of the road surface to be detected, a receiving unit coupled to an optical element for focusing the radiation back-diffused by the road surface and an electronic control and processing unit for receiving signals at output from said receiving unit and for processing them in order to determine the condition of the road surface, on the basis of a reference map. Appearing in said map are the values of the intensity of radiation $I_{ref}$ back-reflected at a reference wavelength and at least one second wavelength. The map is divided into subareas identified beforehand as corresponding to the different conditions of the road surface.

24 Claims, 11 Drawing Sheets

_OPTICAL DEVICE FOR MOTOR VEHICLES, FOR DETECTING THE CONDITION OF THE ROAD SURFACE_

This application claims priority to European Application No. 08425784.9, filed 9 Dec. 2008, the entire contents of which is hereby incorporated by reference.

BACKGROUND OF THE INVENTION

The present invention relates to optical devices that can be used on a motor vehicle for detection of the condition of the road surface, for example, for detecting whether the road surface is dry or wet and/or covered with snow and/or ice.

Devices of this type are already known in the art. For instance, the U.S. Pat. No. 5,497,100 describes a device that makes use of an emitter of electromagnetic radiation having frequencies comprised in the spectral band of microwaves and which analyses the components of the radiation reflected from the road surface, distinguishing whether said surface is dry, wet, or icy, on the basis of the different dielectric constants between these conditions, which affect the reflected radiation.

Other types of devices use the spectral band of the infrared, as described, for example, in the document DE-A-4008280. In this spectral range, in fact, there exist wavelengths that can be selectively absorbed by a wet or icy layer so that, by making the ratio between the signals reflected for the wavelengths of interest, it is possible to identify the road condition. However, with this methodology, even though it is relatively easy to distinguish between a condition of dry road and a condition of road that is not dry, the distinction between a wet condition and an icy condition proves to be more problematical. For this reason, for example in DE-A-4040842, two devices are combined that are able to detect the radiation reflected in the spectral bandwidths of the microwaves and of the infrared. Or else in US2004-204812 there has been proposed the use of temperature sensors, ultrasound sensors, and telecameras. The use of these methodologies is disadvantageous, above all for use on vehicles, on account of the high cost of the device.

SUMMARY OF THE INVENTION

The object of the present invention is to provide an optical device for motor vehicles having a relatively simple and low-cost structure, which can be installed, for example, within a front light assembly or in other suitable points of a vehicle, for example, an automobile or a lorry, or an industrial vehicle in general, said device being able to recognize the condition of the road surface, and in particular being capable of discerning between the conditions of road dry, wet, icy, and covered with snow, supplying also, preferably, a corresponding value of the coefficient of friction that can be associated to the surface detected.

With a view to achieving the above object, the subject of the invention is a device according to claim 1 and a method of detection according to claim 18.

Thanks to the specified characteristics, the invention enables reliable information to be obtained with simple and of low-cost means, which enables discrimination not only between a dry condition and a wet condition of the road surface, but also, for example, between a wet condition and an icy condition or between an icy condition and a condition where the road surface is covered with snow. In particular, the invention is also able to supply, with simple and reliable means, information on the coefficient of friction that can be attributed to the road surface.

The use of the device according to the invention on board a vehicle can be envisaged as a whole either as a safety element, for providing a warning of danger to the driver, or as an element that can be used in the framework of a system for supplying information on the road condition to other vehicles or to road boards or similar bodies, or else as an element designed to supply dynamically a parameter regarding the coefficient of friction of the road surface to systems for stabilization of the vehicle and/or of braking control, such as the so-called ESP, ABS, and ASR.

Preferred and advantageous characteristics of the invention are specified in the annexed dependent claims, the contents of which also forms an integral part of the present description.

BRIEF DESCRIPTION OF THE DRAWINGS

Further characteristics and advantages of the invention will emerge from the ensuing description with reference to the annexed drawings, which are provided purely by way of non-limiting example and in which.

DETAILED DESCRIPTION OF THE INVENTION

Figure 1:
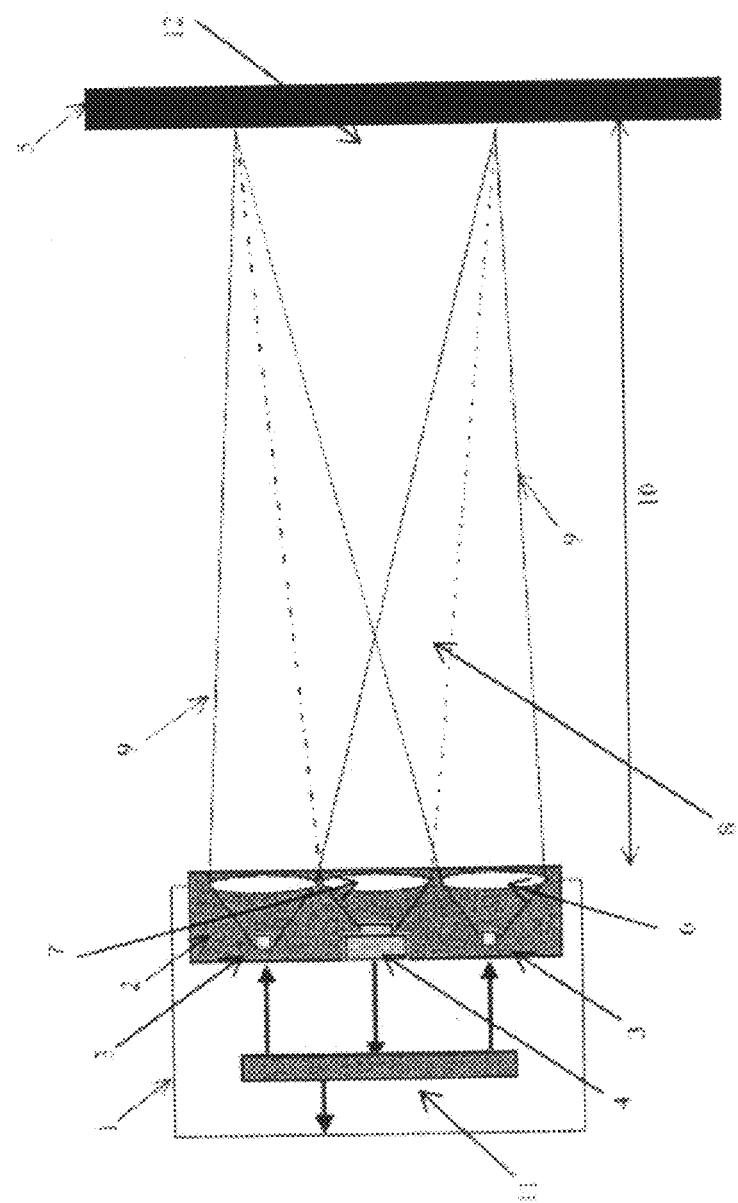
FIG. 1 is a schematic top plan view of an example of embodiment of the device according to the invention.

With reference to FIG. 1, the optical device 1 according to the invention comprises an optical unit 2, which includes a device for emission of radiation made up of at least two sources 3 that are able to emit radiation in the spectral region comprised in the visible and/or near infrared and of optical elements 6, such as lenses, fibres, etc., coupled to said sources 3 in such a way as to direct the radiation emitted by said sources onto a portion of road 12 with beams 9. Said beams are characterized in that, once the height of installation 10 of the device 1 from the road 5 has been established, the beams 9 superimpose on one another in a region 12 so as to light up said portion of road uniformly.

The device moreover includes a receiving unit 4, to which an optical element 7 is coupled, which is able to focus the radiation back-diffused by the portion of road 12 onto the receiving unit 4.

Described hereinafter is the principle of operation of the optical device according to the invention.

Figure 2:
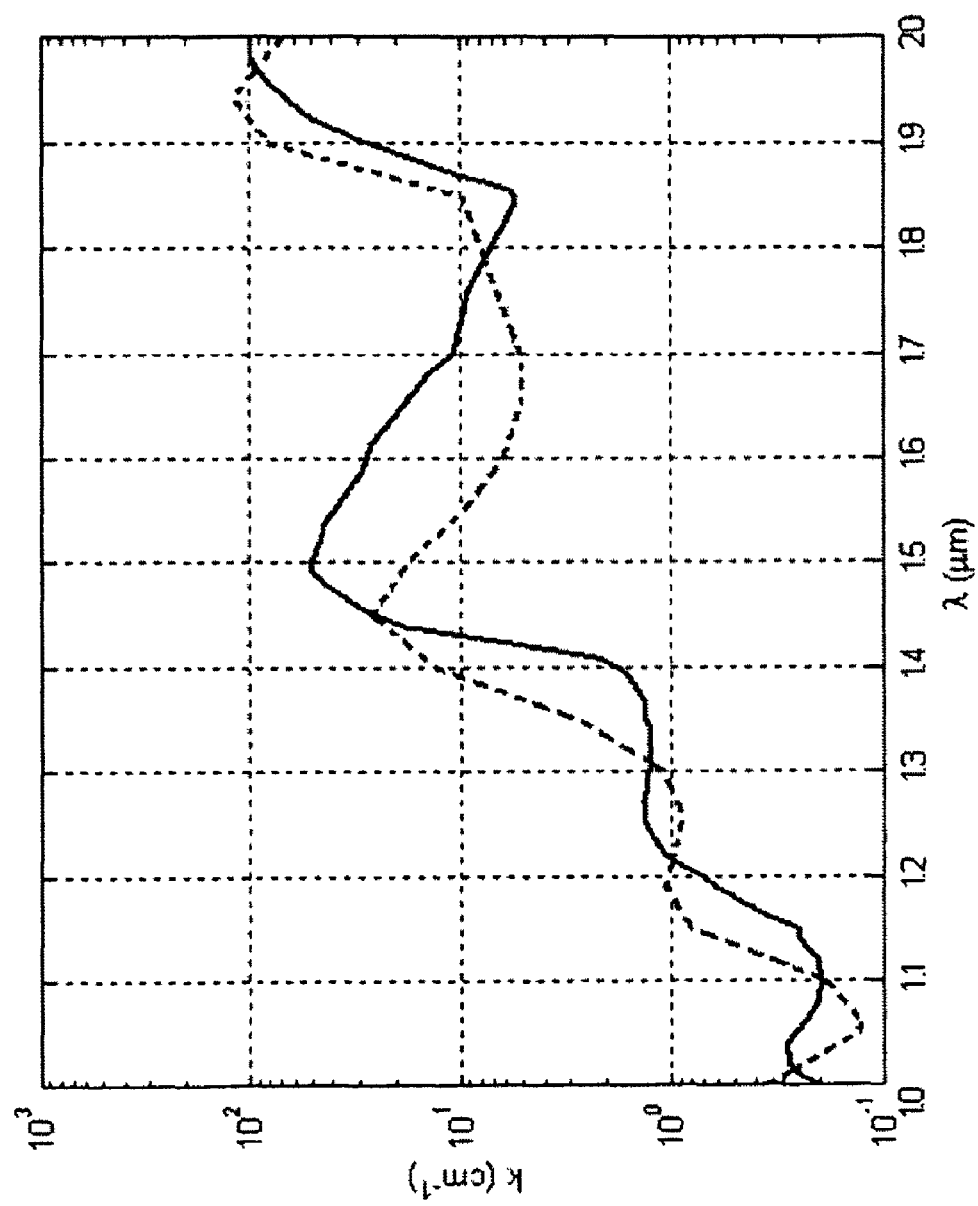
FIG. 2 illustrates a diagram that gives the values of the index of absorption of water and of ice.
Figure 3:
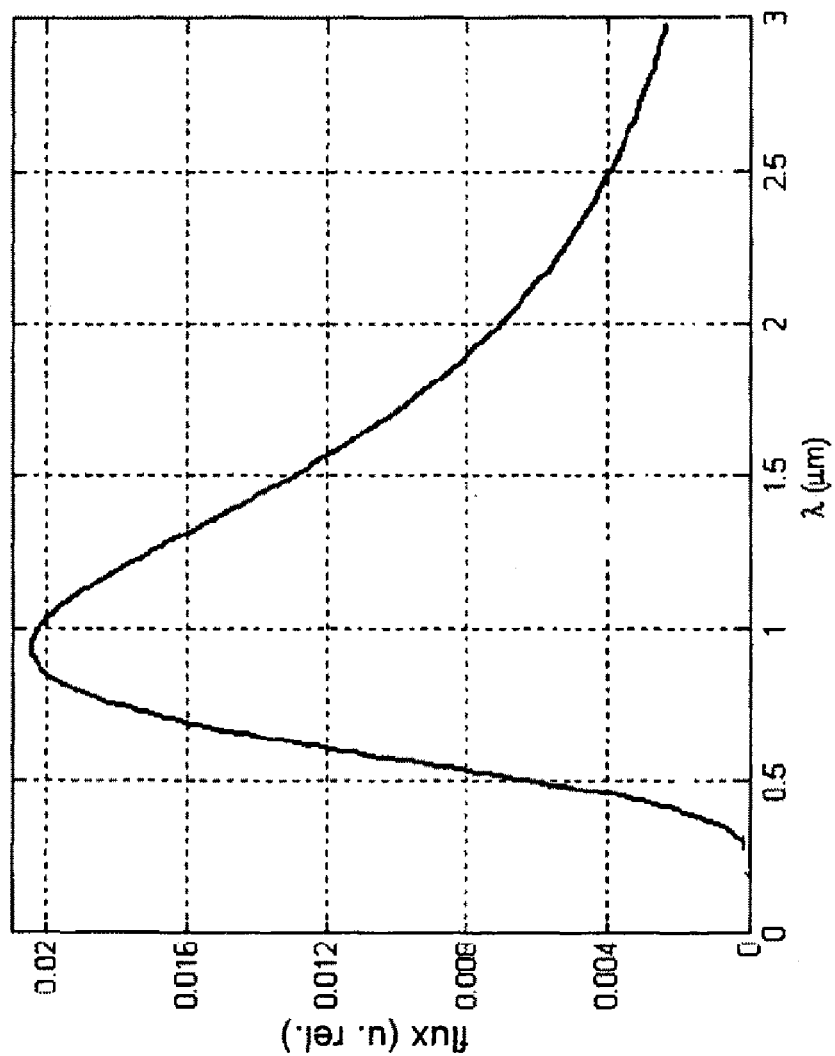
FIG. 3 is a diagram that shows the spectral emission of an incandescent lamp.
Figure 4:
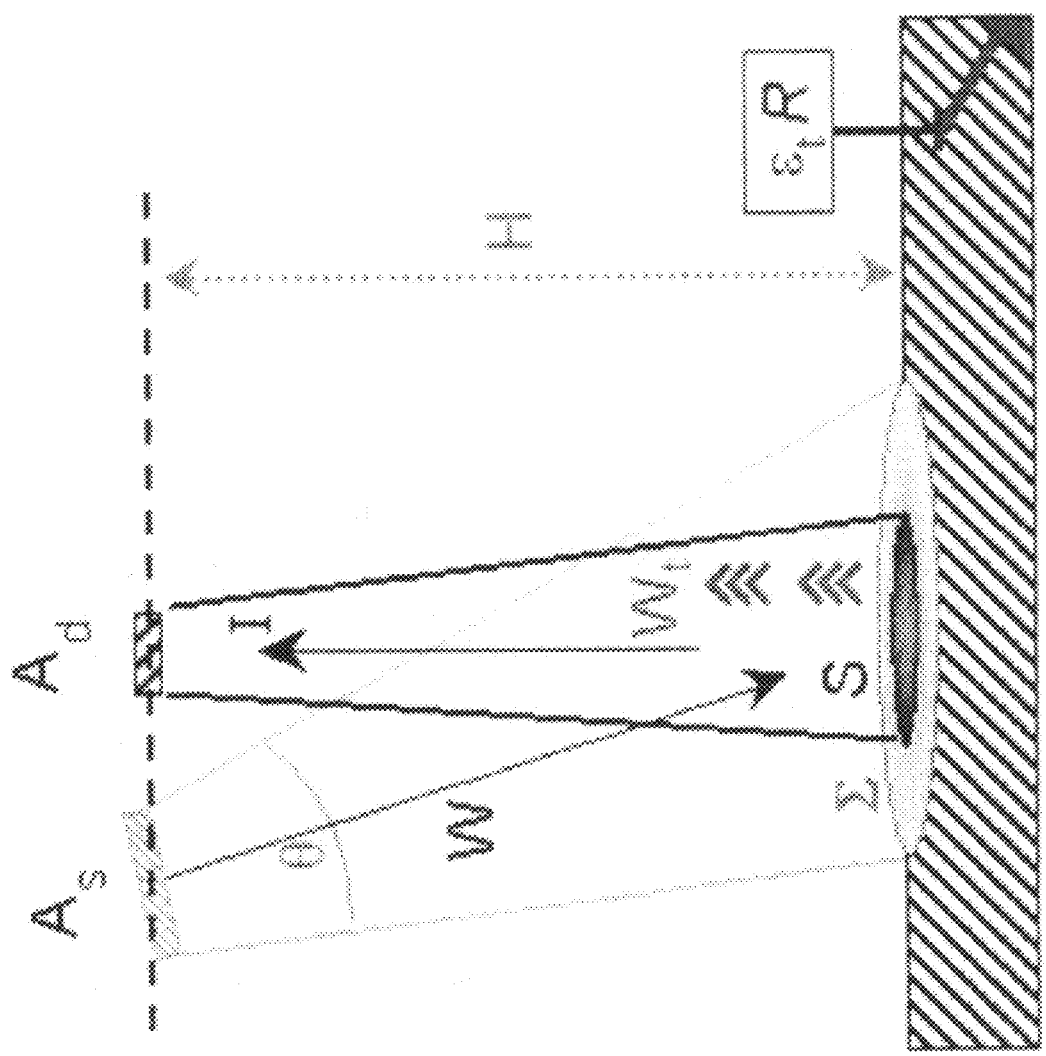
FIG. 4 is a diagram that shows the main quantities characterizing the device according to the invention.

With reference to FIG. 2, it may be noted that the values of the index of absorption of water and of ice present a similar, but not perfectly superimposable, pattern in a spectral region comprised, for example, between 1 μm and 2 μm. This disparity leads to the fact that layers of water and ice absorb, to a different extent, radiation the various wavelengths of which correspond to values of index of absorption for water and ice that are not the same. In particular, there exist values such that the molecules of water or ice are set in rotovibrational excitation and the spectral value of the index of absorption presents local maxima, as, for instance, occurs in the spectral region around 1.5 μm. With reference to FIGS. 3 and 4, consider sending a radiation of light emitted by a source of an incandescent type, the spectrum of emission of which, represented in FIG. 3, will respect Planck's equation:

$$M_{\lambda,e} = \frac{\mathcal{K}_1}{\lambda^5(e^{\mathcal{K}_2/\lambda T} - 1)}$$

$$K_1 = 37418 \text{ W cm}^{-2} \text{ }\mu m^{-4}$$

$$K_2 = 14388 \text{ K }\mu m$$

The parameters that must be considered for characterization of the device are given in FIG. 4, where As is the area of the emitting surface, Ad is the area of the receiving surface, θ is the angle of emission of the radiation leaving the surface As, Σ is the area of the portion of road lit up comprised in the angle of emission and set at the distance H from the emitting and receiving surfaces, R is the reflectance of the asphalt, whilst $\in_t$ is the spectral emissivity of the asphalt, which is a function of the temperature, and finally S is the portion of surface of the asphalt in which the back-diffused radiation is able to reach the area of the receiving surface.

The total flux that is able to reach the receiving surface Ad is given by the sum of two contributions, $\Phi_{lamp}$ and $\Phi_{terr}$, of which the former represents the amount of flux that is emitted by the emitting surface As and is able to reach the receiving surface after being back-diffused by the asphalt, and the latter represents the amount of flux that is emitted directly by the asphalt by grey-body emission and is able to reach the receiving surface, as shown in the following equation:

$$\phi_{tot,asc}(\lambda) = \phi_{lamp} + \phi_{terr} =$$

$$= M_{\lambda,e} R \frac{\Sigma A_s A_d}{4\pi^2 H^4 (1 - \cos\alpha)} + \varepsilon_\lambda^{terr} M_{\lambda,e}^{terr} \frac{SA_d}{2\pi H^2} [\text{W }\mu m^{-1}]$$

Figure 5:
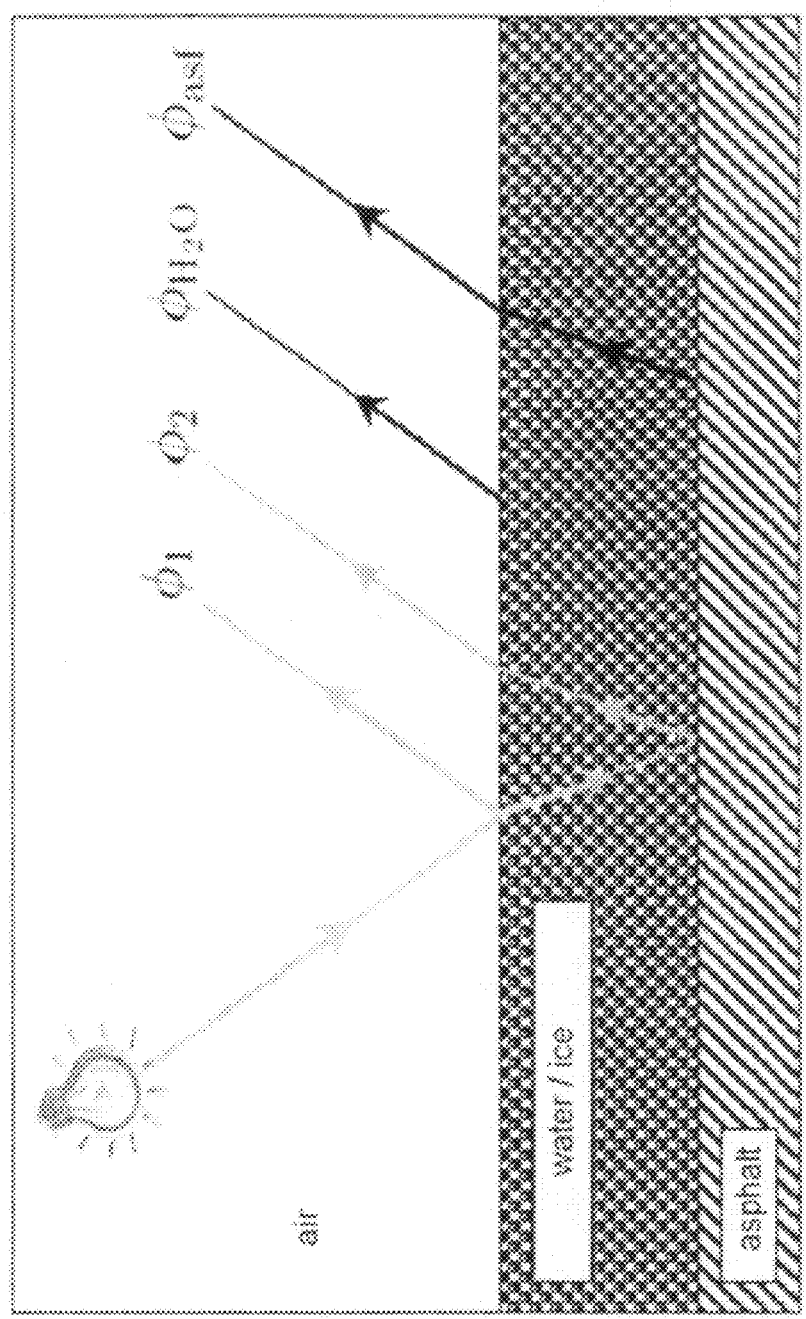
FIG. 5 is a diagram that provides a greater detail of the radiation back-diffused by the road surface and collected by the receiving unit.

With reference to FIG. 5, now consider the more complex case where the road surface is wet or icy. The amount of flux $\Phi_{tot}$ that is able to reach the receiving surface Ad is given by the sum of four contributions, of which the first is the amount emitted by the emitting surface As and reflected by the air-water/ice interface, the second is the amount transmitted by this first interface and subsequently back-diffused by the asphalt, whilst the third and fourth contributions represent the amount of flux emitted by the layer of water/ice (of thickness h) and by the asphalt for a grey body according to Planck's law, as shown in the following equation:

$$\phi_{tot} = \phi_1 + \phi_2 + \phi_{H_2O} + \phi_{asf}$$

$$= M_{\lambda,e}(1 - \tilde{R}_\lambda) R \frac{\Sigma A_s A_d}{4\pi^2 H^4 (1 - \cos\alpha)} e^{-2k_\lambda h} + \phi_{H_2O} + \phi_{asf}$$

The quantity $\tilde{R}_\lambda$, which appears in the formula shown above, represents the spectral reflectance of the water/ice-air interface, whilst $k_\lambda$, which appears as exponent, is the coefficient of spectral absorption, which, linked to the index of spectral absorption, is peculiar to water and ice.

Figure 6:
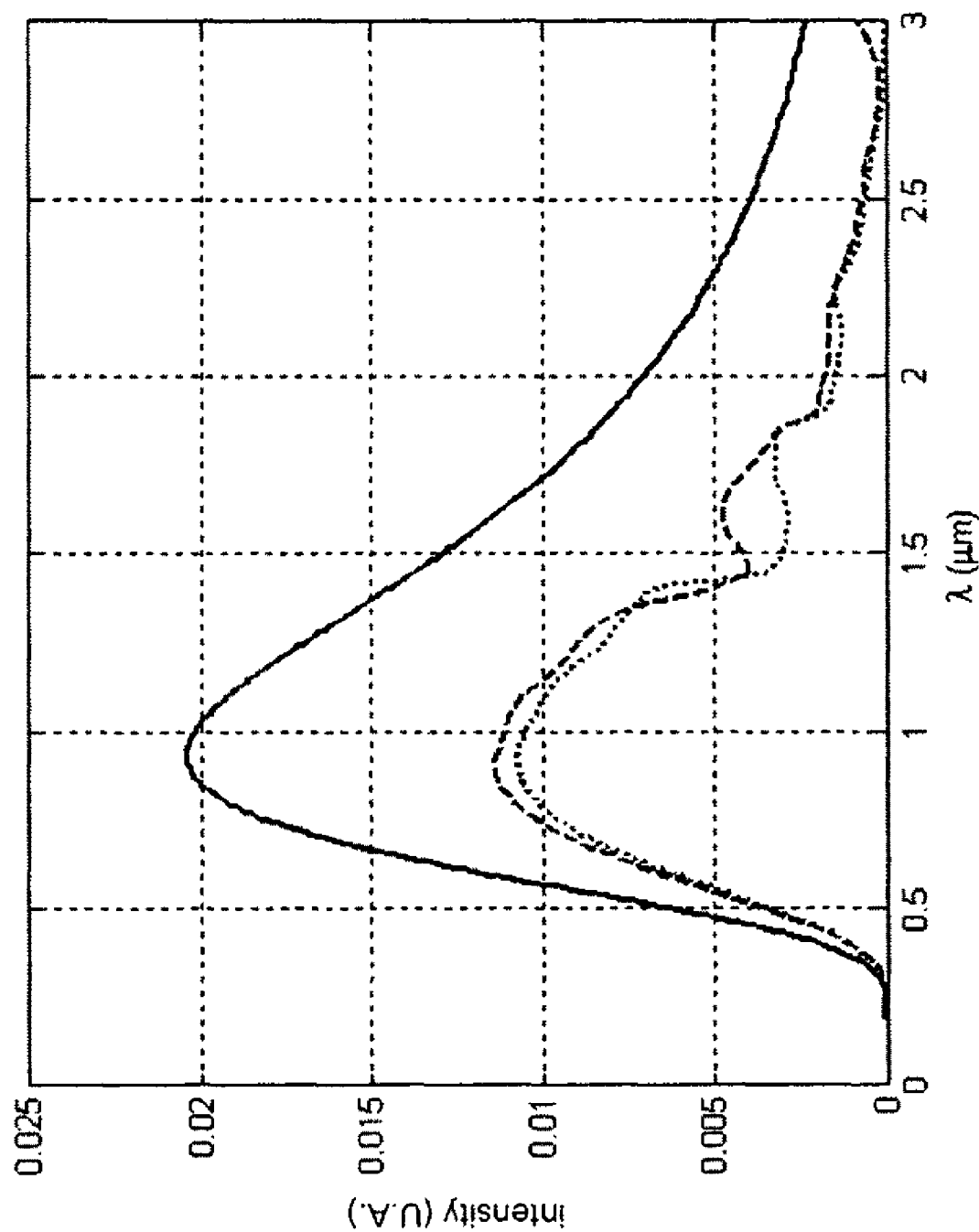
FIG. 6 illustrates a diagram that gives the spectral values of the back-diffused radiation in the case of dry, wet, and icy surfaces.

Appearing in FIG. 6 is a cartesian diagram, in which given on the abscissa is the value of the wavelength and given on the ordinate the value of intensity, expressed in arbitrary units, i.e., the amount of radiation received by the receiving surface Ad according to the formula appearing above. In the present description and in the ensuing claims, the expression "intensity of the radiation received" is understood as referring to said amount. Once again with reference to FIG. 6, the solid line represents the case where a source of emission 3 with a behaviour of an incandescent type emits radiation, which, after being back-diffused by the asphalted surface 5, reaches the receiving unit 4. The dashed line shows, instead, the radiation detected in the case where a layer of water lies on top of the asphalted surface. Finally, the dotted line shows the case where the layer of water is replaced by a layer of ice. As may be noted, in the range of wavelengths considered, the amount of radiation incident on the receiving unit 4 for certain wavelengths is not the same for the different conditions of the road surface. It hence proves possible to discern the condition of the road surface by choosing at least two wavelengths, the first of which has the peculiarity of presenting a corresponding value of intensity that is invariant to a change in road condition, whilst the second has a corresponding value of intensity that can vary sensibly between different road conditions, and by representing the corresponding values of intensity on a cartesian diagram.

Figure 7:
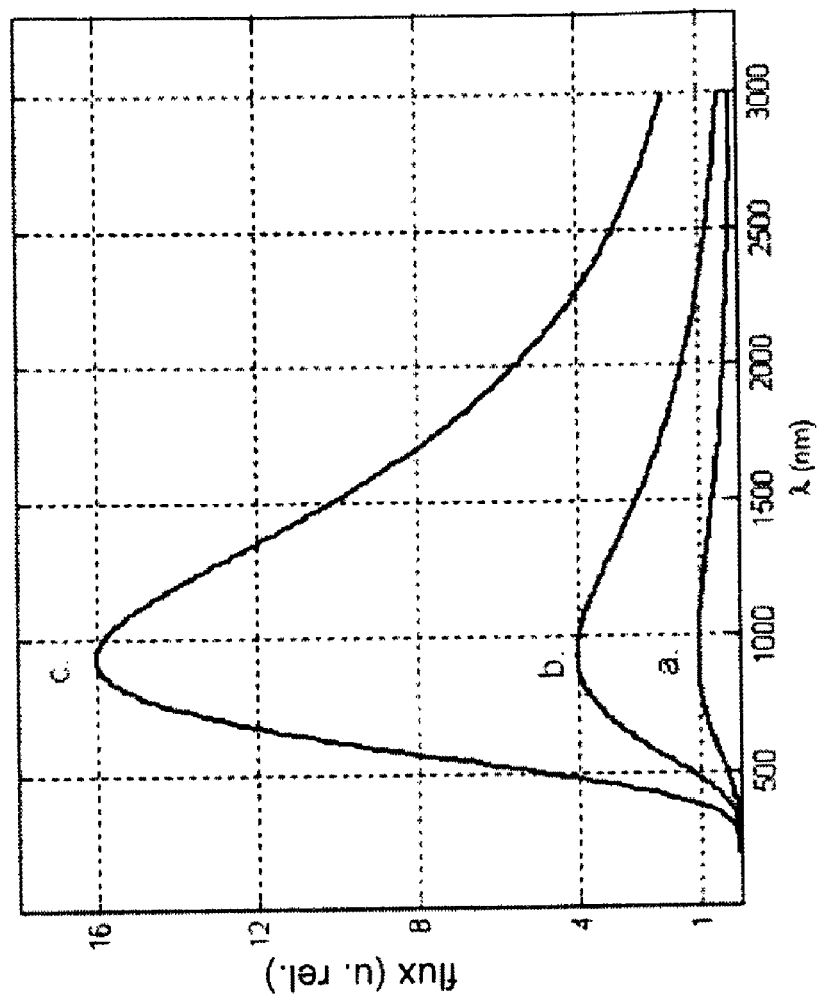
FIG. 7 illustrates a diagram that gives the spectral values of the back-diffused radiation in the case of a dry surface for different heights of installation of the device according to the invention.

The model of the phenomenon described above moreover enables optimization of different parameters, such as, by way of example, the wavelength, the height of installation of the device, or the selection of the ranges of thickness of water and ice for which it is intended to maximize the response of the sensor. Illustrated by way of example with reference to FIG. 7 is the spectral evolution of the radiation received by the receiving surface Ad for different distances from the road surface.

A better discrimination between the signal received by the receiving unit 4 due to the emission by the emission unit 3 and to the back-diffusion by the road surface, with respect to other forms of radiation received once again by the receiving unit 4, can be obtained by means of known techniques, such as, for example, the use of band-pass interferential filters, which are able to select just the wavelengths of interest.

Furthermore, independence with respect to the condition of lighting can also be obtained by means of known techniques, for example, using sources of emission of radiation pulsed at pre-set frequencies and using an electronic filter of a band-pass type that is able to elide the contribution of radiation reflected outside the frequency band selected. In fact, the natural frequencies of the variation of the condition of lighting are rather low (<50 Hz), whilst the frequency at which it is possible to pulse the sources of emission can be of the order of kilohertz.

Figure 8:
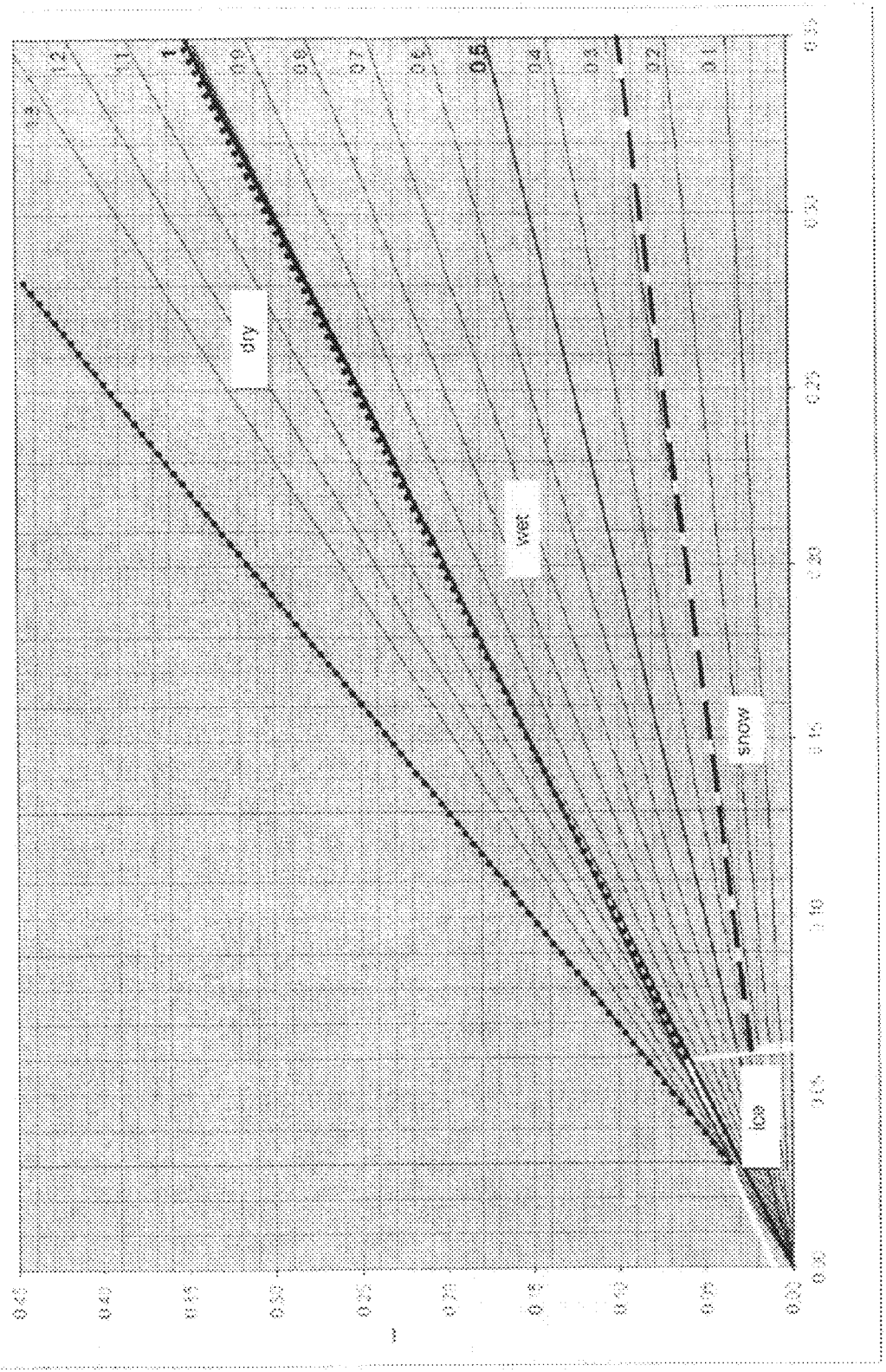
FIG. 8 shows the cartesian plane in which the values of intensity of radiation back-diffused and collected by said receiving unit are plotted and in which the portions of plane defined beforehand for selection of the corresponding road condition are highlighted.

For this reason, with reference once again to FIG. 1, the optical device 1 is made up of an electronic control and processing unit 11, which is able to regulate emission of the sources and define the timing of acquisition of the receiving unit 4, and, by analysing the values of voltage of the receiving unit corresponding to the radiation back-diffused and sent by the emission unit 3, said electronic unit 11 is moreover able to associate to said values a condition of the road (dry, wet, icy, or covered with snow) according to what is shown in FIG. 8.

FIG. 8 shows, in fact, by way of example for two wavelengths, a cartesian diagram, in which appearing on the ordinates are the values of intensity of the radiation back-diffused by the road surface and collected by the receiving unit, which correspond to a wavelength such that the change of road condition causes a change of back-diffused intensity (I), and on the abscissae the values of intensity corresponding to a wavelength such that changes of road condition do not lead to a variation of back-diffused intensity ($I_{ref}$).

The radial lines indicated by values from 0.1 to 1.3 correspond to the values of the ratio between I and $I_{ref}$, whilst the dashed lines identify areas distinguished by different conditions of the road. As may be noted, in the case considered of just two wavelengths, it proves critical to identify uniquely the condition of the road surface exclusively by means of the value of the ratio considered above, given that it is, in particular, not possible to discern the wet/icy conditions, whereas it is still possible to identify correctly the conditions of dry road surface and road covered with snow. The values of intensity corresponding to the wavelengths considered are associated to values of abscissa and ordinate, which define points that, represented in the cartesian diagram, vary their position as a function of said values of abscissa and ordinate (which are functions of the road condition). By means of the division of the cartesian diagram, proposed by way of example in FIG. 8, the fact that the points belong to predefined areas enables determination of the condition of the road surface. The possibility of determining beforehand the division of the regions corresponding to distinct conditions of the road surface lies in the fact that the reflectance of ice proves to be lower than that of water. It follows that an icy surface will reflect less radiation both in the wavelengths where absorption does not occur and in those where there occurs absorption with respect to a wet surface. For this reason, given the same absorption, and hence given the same ratio $I/I_{ref}$ it is possible to discriminate between road conditions.

In the case where a number of sources, associated to the respective wavelengths of emission, equal to three were chosen, the corresponding diagram would be a three-dimensional graph with the regions corresponding to each road condition delimited by the intersection of surfaces. Obviously, by extension, with a number of sources higher than four, it would not be possible to represent a diagram containing the regions corresponding to the road conditions, even though it would in any case remain possible to identify ranges of values that can be obtained from the intersection of hyperplanes.

Figure 9:
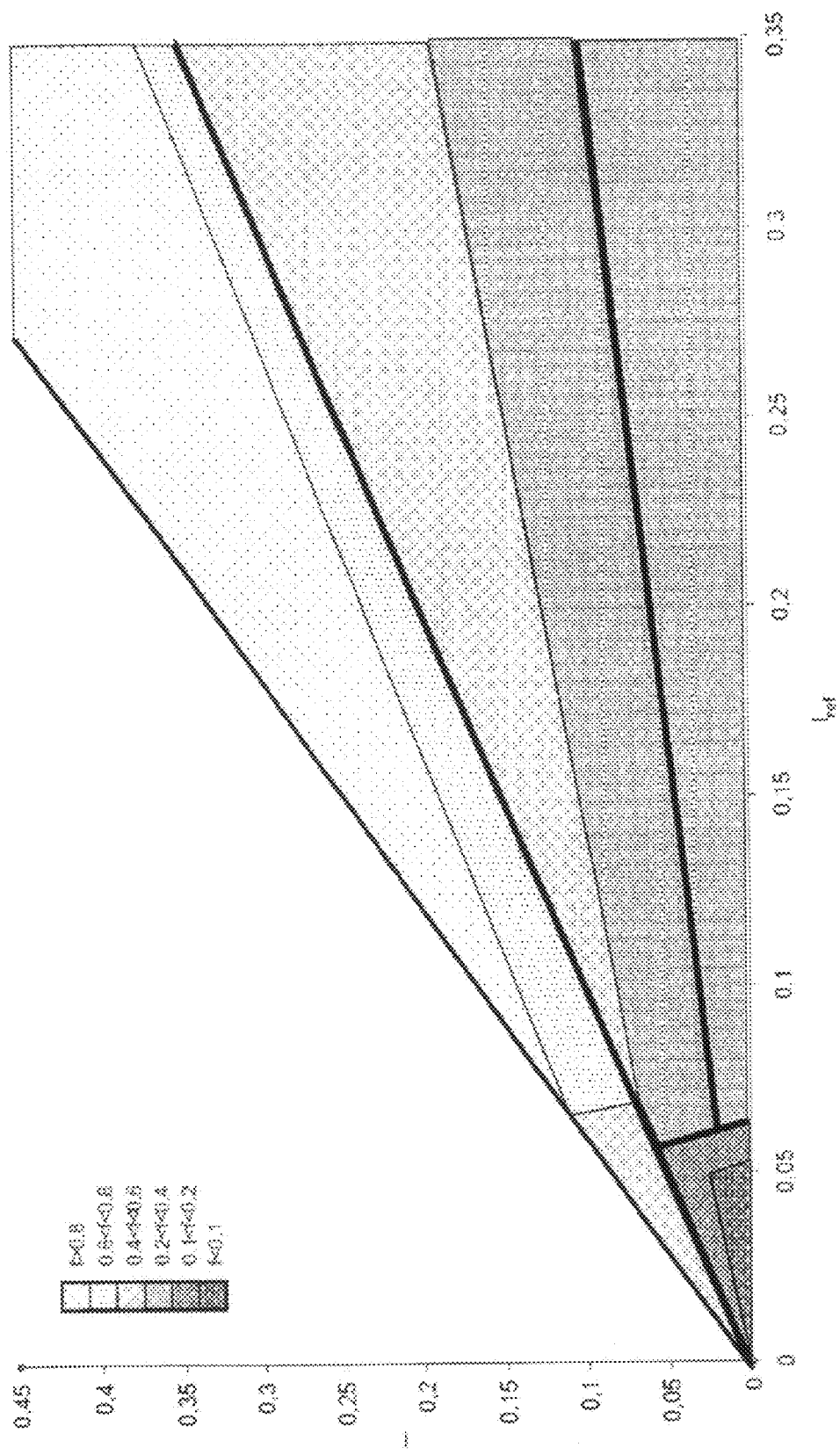
FIG. 9 shows a diagram highlighting portions divided on the basis of different ranges of values of coefficient of friction.

As regards the identification of a corresponding value, or range of values, of coefficient of friction that can be associated to different conditions of the road surface, FIG. 9, which illustrates a possible preferred characteristic of the invention, shows a diagram in which, superimposed on the regions identifying the condition of the road surface delimited by the solid black lines are regions corresponding to intervals of values f of the coefficient of friction. Consequently, the point the co-ordinates of which correspond to the values of intensity, at the two wavelengths selected, back-diffused by the asphalt, identify a road condition and, as subset, a range of values of the coefficient of friction. It should be noted, in fact, how, within a region indicating the road condition, it is possible to identify a number of regions constituting ranges of values of the coefficient of friction. Determination of said regions can be made beforehand and rendered versatile as regards the possibility of modifying, by means of parameterization, the segments delimiting the regions themselves. In this way, slight modifications that become necessary for particular installations of the optical device forming the subject of the invention, can be made by acting on the electronic unit 11, which can likewise have in memory parameters corresponding to different configurations.

Figure 10:
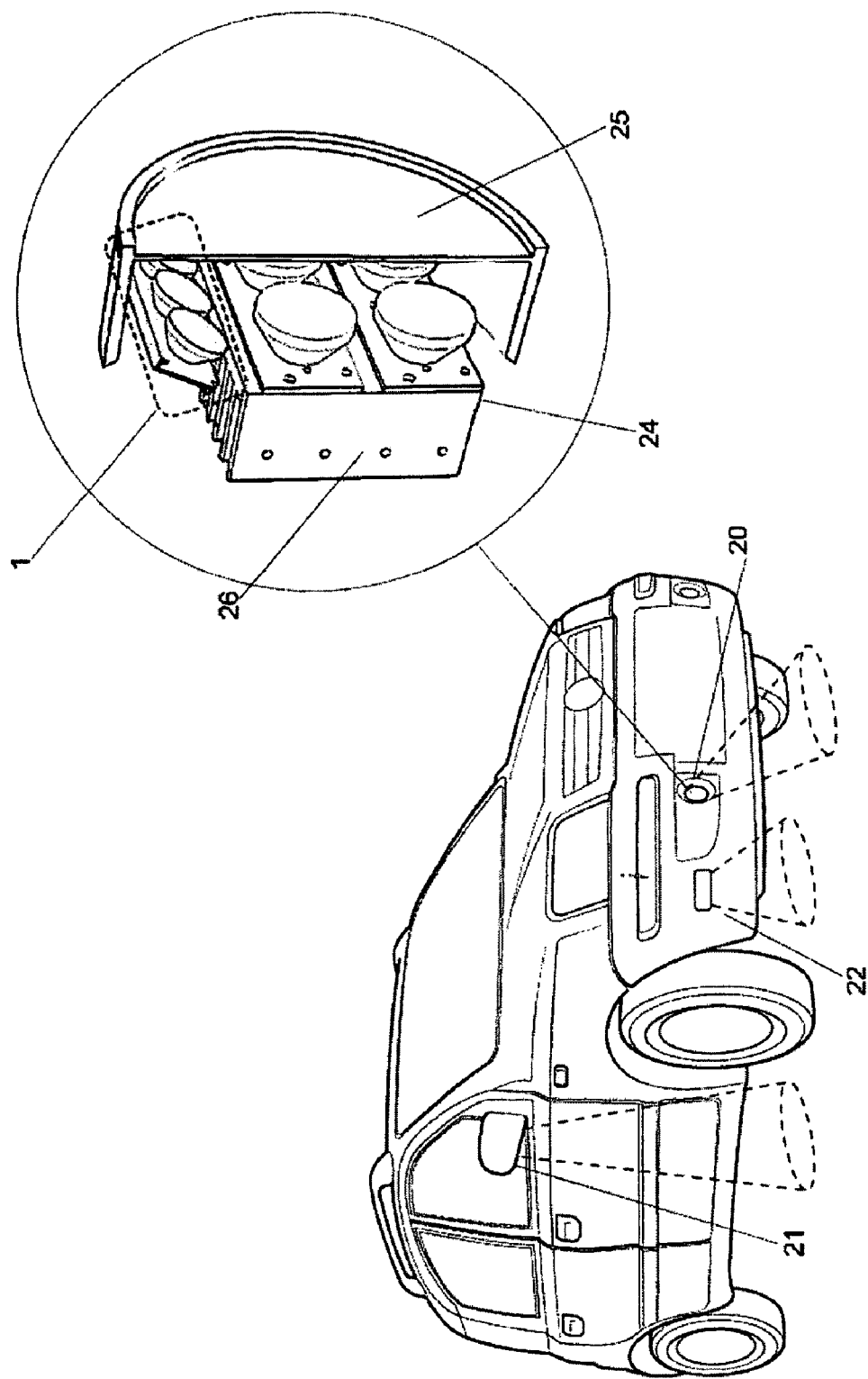
FIG. 10 illustrates possible installations, on board the motor vehicle, of the device of FIG. 1.

A further peculiar characteristic of the present invention is the installation of the optical device on board the vehicle. As is known, in fact, in general optical devices are particularly sensitive to dust and accumulations of dirt on the optical surfaces, which degrade performance and hence limit use thereof. This is particularly true for the use of this type of devices on automobiles, and, consequently, an optimized installation has the same importance as the development of the optical device itself. With reference to FIG. 10, according to a preferred characteristic, the optical device 1 forming the subject of the invention is installed in a position 20 within the compartment reserved to a function of front lighting, such as, for example, a foglight, passing beam/driving beam assembly, or DRL function. Considering that the unit for emission of the beam 3 can be constituted by LED and IRLED sources, the combination of the optical device 1 with a function using LEDs proves to be particularly effective in so far as it enables sharing of the elements of thermal dissipation 26 typically present in said lighting devices. Consequently, a preferred characteristic of the optical device forming the subject of the invention consists in a headlight for motor vehicles 24, preferably using as sources of emission of light LEDs, which are able to perform the function of monitoring the road condition by means of the technique forming the subject of the invention.

The advantages of said position of installation moreover lie in that the device proves to be protected from external agents, the height of installation is never typically greater than 50 cm, with consequent limited power of the sources of radiation, and the measurement of the condition of the road surface can be made in a preventive mode, i.e., on a portion of road not yet traveled along by the vehicle. Furthermore, the glass 25 typically used for protection of the headlight presents characteristics of spectral transmittance such as to guarantee operation of the optical device in question according to what is described. Once again, the headlight can be equipped, according to known techniques, with known means designed for cleaning the protective glass, such as wipers, nozzles for cleaning, nozzles for sending air under pressure, etc. Any possible dust that might have accumulated on the surface of said protective glass, in any case, does not alter the spectral information useful for the purpose of identification of the road condition and of the coefficient of friction, but affects the range of measurement, i.e., the maximum distance within which the optical device is able to carry out the measurement of the road condition. Consequently, it is obvious that, once the position of installation is known, it is possible to choose the sources of emission of radiation with a power such as to ensure proper operation even in the most disadvantageous conditions, thus guaranteeing functionality in any other condition.

According to another preferred characteristic, the optical device is installed in the position 21, in the compartment of the right or left rearview mirror of the vehicle, with a field of view such as to frame a portion of road contiguous to the vehicle. Said solution presents the advantages of a convenient wiring, a position that is protected and subject to a lesser extent to getting dirty and finally to the fact that the radiation back-diffused by the portion of asphalt at a very small angle between the emission unit and the receiving unit 4 is greater than the radiation back-diffused at larger angles, as occurs in the case described previously. The disadvantages lie in a greater distance of the optical device from the road surface, with consequent need for a higher power of the sources of emission of radiation and an impossibility to make a measurement of the road condition of a predictive type.

In a further preferred characteristic, the optical device is installed in the position 22, within the engine compartment, in a lateral position with respect to the centre of the automobile where the radiator is generally positioned, with a field of view such as to frame a portion of road surface underlying the bumpers of the vehicle. Even though said position guarantees a good protection of the optical device, it suffers from more limitations as compared to the solutions illustrated previously. In particular, the temperature of the engine compartment can limit operation thereof or complicate design of the protective casing.

Figure 11:
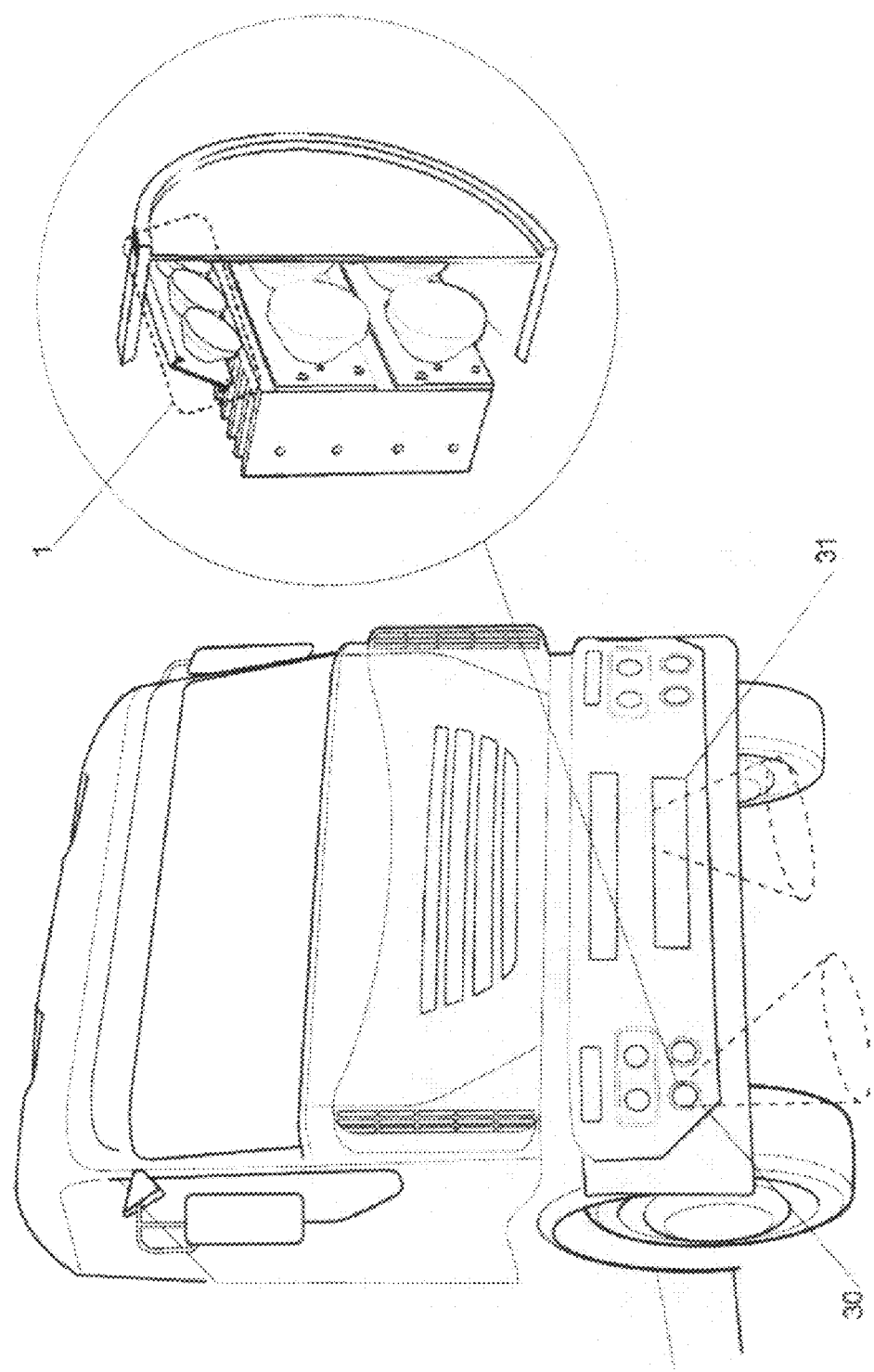
FIG. 11 illustrates some possible installations of the optical device forming the subject of the invention on an industrial vehicle, in the specific case and purely by way of example, a tractor for a semi-trailer.

With reference to FIG. 11, which regards positions of installation of the optical device forming the subject of the invention on a tractor for road use, it is possible to draw considerations similar to those made in the cases of installation on automobiles. In particular, the position 30 regards an installation within a headlight compartment, whilst the position 31 regards a position within the engine compartment.

According to a preferred characteristic, the device for emission of radiation is constituted by semiconductor sources of a LED and IRLED type or else by laser diodes having the characteristic of being able to be pulsed up to frequencies higher than 1 kHz.

According to another preferred characteristic, the device for emission of radiation is constituted by a source of an incandescent or halogen type. In the case of housing of the optical device 1 in the body of the headlight dedicated to front lighting of the vehicle, the source of emission can be the same as the one dedicated to performing the function of lighting, provided that optical elements 6 are used, designed to shape part of the beam of radiation emitted by the source in order to direct it onto a portion of road 12.

In order to guarantee the necessary timing of modulation of the intensity emitted by the source, an element suitable for this purpose, such as, for example, an optical chopper, must be positioned within the optical unit 2. Since the emission device, in this case, would send a beam of radiation that comprises all the spectral components, the receiving unit 4 must be made up of at least two distinct elements coupled to optical filters such as to select the reception of the radiation associated to just the wavelengths of interest.

According to a preferred characteristic, the sensitive element constituting the receiving unit 4 is a silicon photodiode with a high spectral response in the near infrared or a silicon PIN photodiode characterized by a high sensitivity at high frequencies.

According to another preferred characteristic, the sensitive element constituting the receiving unit 4 is an InGaAs PIN photodiode characterized by a high spectral response from 0.9 µm to 1.7 µm or else up to 2.5 µm.

According to a further preferred characteristic, the optical device 1 is pre-arranged so as to supply the data on the condition of the road surface and coefficient of friction in correlation with the value of the ambient-temperature sensor in any case installed on a vehicle for the air-conditioning function. The data can be compared according to known decision strategies in a dedicated electronic unit (ECU), or else in a control unit on board the vehicle, or else the temperature datum can be supplied to the electronic control and processing unit 11.

According to a further preferred characteristic, the optical device 1 is characterized in such a way as to supply the data on the condition of the road surface and coefficient of friction in correlation with the measurement of the temperature of the road surface made at a distance according to known techniques by means of thermoelectric or pyroelectric sensors. The same considerations made previously apply as regards the strategies of decision and the architecture of electronic management.

According to a further preferred characteristic, the optical device 1 is characterized in such a way as to supply the data on the condition of the road surface and coefficient of friction in correlation with the data supplied by a rain sensor commonly installed on board the vehicle. Also in this case, the same considerations made previously apply as regards the strategies of decision and the architecture of electronic management.

According to a further preferred characteristic, the optical device 1 is characterized in such a way as to supply the data on the condition of the road surface and coefficient of friction in correlation with the data acquired by a telecamera for detection of the scene in front of the vehicle, in particular the data of estimation of the condition of wet road surface.

According to a preferred characteristic, the optical device 1 is characterized in that it uses two sources of emission of radiation 3, associated to two distinct wavelengths, and a receiving unit 4 able to receive and distinguish, by associating the intensity of the radiation back-diffused by the portion of asphalt, the corresponding source of emission. In this configuration, the measurement is made in sequential mode, the contribution of the radiation back-diffused by the sources of emission in at least two successive instants of time being distinct.

According to another preferred characteristic, the optical device 1 is characterized in that it uses two sources of emission of radiation 3 and two receiving units 4, each designed to receive the radiation emitted by a source of emission of radiation. In this configuration, the measurement is made in an instantaneous mode, given that the reception of the radiation is made at the same instant in time.

According to another preferred characteristic, the optical device 1 is characterized in that it uses a source of emission of radiation 3 comprising the whole spectrum of wavelengths of interest, and two radiation-receiving units 4, each associated to an optical filter designed to select the pre-defined wavelength (in addition to the optical element for shaping of the beam of radiation 6).

According to another preferred characteristic, the optical device 1 is characterized in that it uses a source of emission of radiation 3 comprising the whole spectrum of wavelengths of interest associated to an optical element, which is designed to separate into at least two optical channels the radiation of emission, said optical channels being characterized in that they are associated to optical filters for selection of the pre-defined wavelength. The optical device 1 is moreover characterized by a radiation-receiving unit 4 for receiving the radiation back-diffused by the portion of asphalt operating in sequential mode. An optical device for modulation of the intensity must moreover be provided either in the emission unit 3 or in the receiving unit 4.

According to another preferred characteristic, the optical device 1 is characterized in that it uses, as in the case of the previous characteristic, a unit for emission of radiation associated to optical elements for separation and selection of the pre-defined wavelengths, and by two receiving units 4 (each associated to the corresponding pre-defined wavelength of emission for receiving radiation back-diffused by the portion of asphalt, which operate in an instantaneous mode.

Of course, without prejudice to the principle of the invention, the details of construction and the embodiments may vary widely with respect to what is described and illustrated herein purely by way of example, without thereby departing from the scope of the present invention.

Obviously, falling, for example, within the scope of the present invention, in so far as it is equivalent to the solution claimed, is the case where the emission device sends a beam of radiation comprising all the spectral components, and the receiving unit is made up of at least two distinct elements coupled to optical filters such as to select reception of the radiation associated to just the wavelengths of interest.

What is claimed is:

1. An optical device for a motor vehicle, designed to detect the condition of a road surface, comprising:
    a unit for an emission of electromagnetic radiation in the direction of the road surface to be detected;
    a receiving unit coupled to an optical element for focusing the electromagnetic radiation back-diffused by the road surface;
    an electronic control and processing unit, designed to receive signals at output from said receiving unit and to process the signals in order to determine the condition of the road surface,
    wherein:
    said unit for emission is able to emit electromagnetic radiation in a spectral region of the visible and/or the near infrared;
    said control and processing unit is provided for detecting:
    both an intensity $I_{ref}$ of the electromagnetic radiation back-reflected at a first wavelength, considered as reference wavelength,
    and an intensity I of the electromagnetic radiation back-reflected at at least one second wavelength,
    said control and processing unit being programmed in such a way that, to a given pair of values of the intensity of electromagnetic radiation I, $I_{ref}$ thus detected there is made to correspond a given condition of the road surface on a basis of a reference-map;
    wherein said first wavelength is a wavelength at which the intensity of the back-diffused light from the road is invariant to a change of road condition,
    wherein said second wavelength is a wavelength at which the intensity of the back-diffused light from the road varies between different road conditions,
    wherein said reference is a reference map, in a form of a cartesian plane in which values of the intensity of electromagnetic radiation $I_{ref}$ back-reflected at the reference wavelength appear on a first cartesian axis, the values of the intensity of electromagnetic radiation I back-reflected at the second wavelength appear on a second cartesian axis, wherein said cartesian plane is divided into subareas identified beforehand as corresponding to different conditions of the road surface, and wherein boundary lines that divide said subareas from one another comprise both:
        portions of a straight line converging radially towards a common origin of the cartesian plane, and
        portions of a straight line oriented transversely with respect to said portions of a straight line converging radially and
    wherein one of said portions of a straight line which are oriented transversely with respect to said portions of a straight line converging radially separates a region of the map corresponding to presence of ice on the road surface from regions corresponding to the presence of water or snow on the road surface.

2. The device according to claim 1, wherein said electronic control and processing unit is also designed to regulate said unit for emission.

3. The device according to claim 1, wherein said reference map is pre-determined with subareas each corresponding to a condition of the road surface: dry, wet, icy, and covered with snow.

4. The device according to claim 1, wherein said reference map is pre-determined with subareas respectively corresponding to a plurality of different ranges of values of the coefficient of friction of the road surface.

5. The device according to claim 1, wherein the device is pre-arranged for being installed inside a front light assembly of a motor vehicle.

6. The device according to claim 1, wherein the device constitutes a motor-vehicle headlight, said headlight being thus able to perform both the function of headlight and the function of detector of the condition of the road surface.

7. The device according to claim 6, wherein a source of light of the headlight constitutes at least part of said unit for emission.

8. The device according to claim 1, wherein the device is pre-arranged for being installed within a body of an external rearview mirror of a motor vehicle.

9. The device according to claim 1, wherein the device is pre-arranged for being installed within an engine compartment of a motor vehicle.

10. The device according to claim 5, wherein at least one source light is a same source dedicated to a function of lighting, and, in the source, optical elements are provided, designed to shape part of a beam of electromagnetic radiation emitted by the source in order to direct the beam onto a portion of road.

11. The device according to claim 10, wherein the device comprises an optical chopper positioned within a light assembly.

12. The device according to claim 1, wherein said unit for emission comprises one or more light sources chosen from among LEDs, IRLEDs, laser diodes, incandescence sources, and halogen sources coupled to an optical chopper.

13. The device according to claim 1, wherein a sensitive element constituting the receiving unit is chosen from between:
    a silicon photodiode with high spectral response in the near infrared or a silicon PIN photodiode characterized by a high sensitivity at high frequencies; and
    an InGaAs PIN photodiode characterized by a high spectral response from 0.9 µm to 1.7 µm or else up to 2.5 µm.

14. The device according to claim 1, wherein the optical device is pre-arranged so as to supply data on the condition of the road surface and/or on a coefficient of friction in correlation with a signal emitted by an ambient-temperature sensor.

15. The device according to claim 1, wherein the optical device is pre-arranged so as to supply data on the condition of the road surface and/or on a coefficient of friction in correlation with a measurement of a temperature of the road surface made at a distance by means of thermoelectric or pyroelectric sensors.

16. The device according to claim 1, wherein the optical device is pre-arranged so as to supply data on the condition of the road surface and/or on a coefficient of friction in correlation with the data supplied by a rain sensor installed on board the motor vehicle.

17. The device according to claim 1, wherein the optical device is pre-arranged so as to supply data on the condition of the road surface and/or on a coefficient of friction in correlation with data acquired by a telecamera for detecting a scene in front of the motor vehicle, in particular the data of estimation of the condition of wet road surface.

18. The device according to claim 1, wherein comprises two sources of emission of electromagnetic radiation, associated to two distinct wavelengths, and a receiving unit able to receive and distinguish, by associating an intensity of the electromagnetic radiation, radiation back-diffused by a portion of asphalt, a corresponding source of emission, a measurement being made in a sequential mode, contributions of the electromagnetic radiation, back-diffused by sources of emission in at least two successive instants of time being distinct.

19. The device according to claim 1, wherein the device comprises two sources of emission of electromagnetic radiation and two receiving units, each designed to receive electromagnetic radiation emitted by a source of emission of electromagnetic radiation, measurements being made simultaneously.

20. The device according to claim 1, wherein the device comprises a source of emission of electromagnetic radiation comprising a whole spectrum of wavelengths of interest and two radiation-receiving units, each associated to an optical filter, designed to select a pre-defined wavelength.

21. The device according to claim 1, wherein the device comprises a source of emission of electromagnetic radiation comprising a whole spectrum of wavelengths of interest, associated to an optical element designed to separate into at least two optical channels the electromagnetic radiation of emission, said optical channels being characterized in that they are associated to optical filters for selection of a pre-defined wavelength and in that there is provided a single radiation-receiving unit operating in sequential mode, or else in that there are provided two receiving units operating simultaneously.

22. A method for detecting on board a motor vehicle a condition of a road surface on which the motor vehicle is travelling, which envisages:
   emitting electromagnetic radiation in the direction of the road surface to be detected; and
   receiving and analysing the electromagnetic radiation back-diffused by the road surface, in order to determine the condition of the road surface,
   wherein:
   the electromagnetic radiation emitted towards the road surface is in a spectral region of the visible and/or near infrared;
   said analysis of the back-reflected electromagnetic radiation is made by detecting:
   both an intensity $I_{ref}$ of the electromagnetic radiation back-reflected at a first wavelength, considered as reference wavelength;
   and an intensity I of the electromagnetic radiation back-reflected at at least one second wavelength; and
   to a given pair of values of an intensity of electromagnetic radiation I, $I_{ref}$ thus detected there is made to correspond a given condition of the road surface on a basis of a reference,
   wherein said first wavelength is a wavelength at which the intensity of the back-diffused light from the road is invariant to a change of road condition,
   wherein said second wavelength is a wavelength at which the intensity of the back-diffused light from the road varies between different road conditions,
   wherein said reference is a reference map, in a form of a cartesian plane in which values of the intensity of electromagnetic radiation $I_{ref}$ back-reflected at the reference wavelength appear on a first cartesian axis, the values of the intensity of electromagnetic radiation back-reflected at the second wavelength appear on a second cartesian axis, in which said cartesian plane is divided into subareas identified beforehand as corresponding to different conditions of the road surface, and in which the boundary lines that divide said subareas from one another comprise both:
      portions of a straight line converging radially towards a common origin of the cartesian plane, and
      portions of a straight line oriented transversely with respect to said portions of a straight line converging radially,
   wherein one or said portions of a straight line which are oriented transversely with respect to said portions of a straight line converging radially separates a region of the map corresponding to presence of ice on the road surface from regions corresponding to the presence of water or snow on the road surface.

23. The method according to claim 22, wherein said reference map is pre-determined with subareas each corresponding to a condition of the road surface: dry, wet, icy, and covered with snow.

24. The method according to claim 22, wherein said reference map is pre-determined with subareas respectively each corresponding to a plurality of different ranges of values of a coefficient of friction of the road surface.

* * * * *